United States Patent
Hong et al.

(10) Patent No.: US 12,404,229 B2
(45) Date of Patent: Sep. 2, 2025

(54) PREPARATION METHOD FOR TRANS-CYCLOBUTANE-O-DICARBOXYLIC ACID ESTER AND DERIVATIVE THEREOF

(71) Applicant: JILIN ASYMCHEM PHARMACEUTICALS CO., LTD., Jilin (CN)

(72) Inventors: Hao Hong, Morrisville, NC (US); Enxuan Zhang, Tianjin (CN); Jiangping Lu, Tianjin (CN); Fuliang Wei, Tianjin (CN); Guanda Che, Tianjin (CN); Mingjie Feng, Tianjin (CN)

(73) Assignee: JILIN ASYMCHEM PHARMACEUTICALS CO., LTD., Jilin (CN)

( * ) Notice: Subject to any disclaimer, the term of this patent is extended or adjusted under 35 U.S.C. 154(b) by 700 days.

(21) Appl. No.: 17/755,254

(22) PCT Filed: Oct. 25, 2019

(86) PCT No.: PCT/CN2019/113428
§ 371 (c)(1),
(2) Date: Apr. 25, 2022

(87) PCT Pub. No.: WO2021/077424
PCT Pub. Date: Apr. 29, 2021

(65) Prior Publication Data
US 2022/0380292 A1 Dec. 1, 2022

(51) Int. Cl.
*C07C 67/34* (2006.01)
(52) U.S. Cl.
CPC .......... *C07C 67/34* (2013.01); *C07C 2601/04* (2017.05)
(58) Field of Classification Search
CPC ............................ C07C 67/333; C07C 69/74
USPC ....................................................... 560/123
See application file for complete search history.

(56) References Cited

FOREIGN PATENT DOCUMENTS

| CN | 101044108 A | 9/2007 |
| CN | 101180272 A | 5/2008 |
| WO | 2005118656 A2 | 12/2005 |
| WO | 2005118656 A3 | 1/2006 |

OTHER PUBLICATIONS

Blomquist, A.T. et al., "Synthesis of some conjugated cyclobutane polyolefins and their 1, 2-cycloaddition to tetracyanoethylene", Journal of the American Chemical Society, vol. 81, Feb. 5, 1959, ISSN:0002-7863, pp. 667-672.
Buchman, Edwin R. et al., "Cyclobutane derivatives. I The degradation of cis- and trans-1, 2-cyclobutanedicarboxylic acids to the corresponding diamines", Journal of the American Chemical Society, vol. 64, Dec. 31, 1942, ISSN:0002-7863; pp. 2696-2700.

*Primary Examiner* — Ana Z Muresan
(74) *Attorney, Agent, or Firm* — NKL Law; Allen Xue

(57) ABSTRACT

A preparation method for a trans-cyclobutane-o-dicarboxylic acid ester and a derivative thereof includes the following steps: in an organic solvent, catalyzing a substrate with a structure as shown in a structural formula I by using organic alkali at 50-90° C. so as to generate isomerization, acquiring the trans-cyclobutane-o-dicarboxylic acid ester or the derivative thereof, herein the structural formula I is as follows:

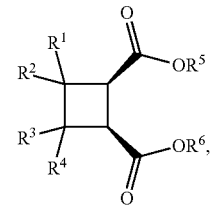

Each $R^1$, $R^2$, $R^3$ and $R^4$ is independently one of hydrogen or an alkyl of $C_1$-$C_5$, and each of $R^5$ and $R^6$ is independently one of alkyl of $C_1$-$C_{10}$ and benzyl.

14 Claims, No Drawings

PREPARATION METHOD FOR TRANS-CYCLOBUTANE-O-DICARBOXYLIC ACID ESTER AND DERIVATIVE THEREOF

TECHNICAL FIELD

The present disclosure relates to the preparation field of trans-cyclobutane-o-dicarboxylic acid ester compounds, in particular to a preparation method for trans-cyclobutane-o-dicarboxylic acid ester and a derivative thereof.

BACKGROUND

Trans-cyclobutane-o-dicarboxylic acid ester compounds are an intermediate raw material for many active pharmaceutical ingredients, such as an antidepressant, an anxiolytic, and especially a chemotherapeutic drug, and are also a precursor of some nano-structured mixed materials, and the market demand is large.

At present, the trans-cyclobutane-o-dicarboxylic acid ester compounds are mainly obtained by isomerization of cis-cyclobutane-o-dicarboxylic acid ester compounds, and routes of the isomerization of the cis-cyclobutane-o-dicarboxylic acid ester compounds mainly include the following several routes:

Photocatalysis: A configuration may be reversed by using a photosensitizer to transfer energy under light. This method needs to screen the photosensitizer, the light intensity, a wavelength and a solvent, a required device is high in cost, and the screening workload is large, the research and development cycle is long, the production capacity is low, and the energy consumption is high.

Acid catalysis: A substrate is dissolved in a concentrated acid (concentrated hydrochloric acid or concentrated sulfuric acid) and it is refluxed for a long time, so that the configuration is reversed. This method requires concentrated acid reflux, and the post-treatment needs to neutralize a large amount of the concentrated acid, so that a large amount of three wastes are generated, it is not beneficial to scale-up production, the reaction time is longer (about 160 h), and the conversion rate is less than 80%.

It may be seen that in an existing technology, the photocatalytic isomerization is relatively high in reaction cost, and the scale-up production may not be achieved due to the limited light conditions; and the acid-catalyzed isomerization requires the use of the concentrated acid as a solvent in a reaction system, a large amount of three wastes are generated in the post-treatment, and the reaction conditions are harsh, a long time (−160 h) reflux reaction is required at a higher temperature (−100 DEG C.), it is also not beneficial to the scale-up production. In addition, because the conversion rate is relatively low, a post-treatment product is not easy to separate, and the target product loss is larger, so that an overall yield is <60%.

SUMMARY

A main purpose of the present disclosure is to provide a preparation method for a trans-cyclobutane-o-dicarboxylic acid ester and a derivative thereof, as to solve a problem in an existing technology that an isomerization method of cyclobutane-o-dicarboxylic acid ester compounds is not suitable for a scale-up production application.

In order to achieve the above purpose, according to one aspect of the present disclosure, a preparation method for a trans-cyclobutane-o-dicarboxylic acid ester and a derivative thereof is provided, including: in an organic solvent, catalyzing a substrate with a structure as shown in a structural formula I by using organic alkali at 50-90 DEG C. so as to generate isomerization, acquiring the trans-cyclobutane-o-dicarboxylic acid ester or the derivative thereof, herein the structural formula I is as follows:

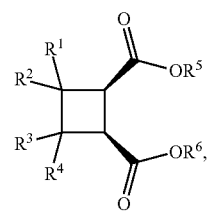

each of $R^1$, $R^2$, $R^3$ and $R^4$ is independently arbitrary one of hydrogen or an alkyl of $C_1$-$C_5$, and each of $R^5$ and $R^6$ is independently arbitrary one of alkyl of $C_1$-$C_{10}$ and benzyl.

Further, the above organic alkali is selected from arbitrary one or more of alkoxide, preferably the alkoxide is sodium alkoxide and potassium alkoxide, further preferably the alkoxide is alkyl alkoxide of $C_1$-$C_5$, and more preferably the alkoxide is sodium methylate, sodium ethoxide, sodium tert-butoxide, and potassium tert-butoxide.

Further, a mole ratio of the above organic alkali and the substrate is 2.5:1-3.0:1.

Further, the above organic solvent is an alcohol solvent, and preferably the organic solvent is arbitrary one of methyl alcohol, ethyl alcohol, tert-butyl alcohol, and isopropyl alcohol.

Further, a volume ratio of the above organic solvent and the substrate is 2:1-5:1.

Further, in the above organic solvent, the organic alkali is used for catalyzing the substrate at 60-70 DEG C. so as to generate the isomerization.

Further, the above preparation method includes the following steps: enabling the substrate to be dissolved in a part of the organic solvent, to form first solution; enabling the organic alkali to be dissolved in the other part of the organic solvent, to form second solution; after cooling the first solution to −5-10 DEG C., mixing with the second solution, to obtain a system to be reacted; and warming the system to be reacted to 60-70 DEG C. and heat-preserving for 1-3 hours so that the substrate generates the isomerization, to obtain a product system containing the trans-cyclobutane-o-dicarboxylic acid ester or the derivative thereof.

Further, the above preparation method further includes the following steps: after cooling the product system to 20-30 DEG C., adjusting a pH value of the product system to 6-7, to obtain a quenching system; extracting the trans-cyclobutane-o-dicarboxylic acid ester or the derivative thereof in the quenching system by using an extracting agent, to obtain an extract; and removing the extracting agent in the extract, to obtain the trans-cyclobutane-o-dicarboxylic acid ester or the derivative thereof.

Further, a diluted hydrochloric acid or a diluted nitric acid is used for adjusting the pH value of the product system, and preferably the extracting agent is arbitrary one of methyl tertiary butyl ether, n-hexane and dibutyl ether.

Further, in the above structural formula I, the $R^1$, the $R^2$, the $R^3$ and the $R^4$ are the same and are the hydrogen or the methyl, and the $R^5$ and the $R^6$ are the same and selected from arbitrary one of the alkyl of $C_1$-$C_5$ and benzyl.

A technical scheme of the present disclosure is applied, the present application uses the organic alkali as a catalyst to catalyze the trans-cyclobutane-o-dicarboxylic acid ester with the structural formula I or the derivative thereof at 50-90 DEG C. so as to generate an isomerization reaction, the process steps are shortened by one-step isomerization and efficient and simple. Reaction conditions are mild, and a special device is not required.

Therefore, it is beneficial to scale-up production. Moreover, a substrate conversion rate and a product yield may be adjusted by adjusting the amount of reagents and the reaction temperature. Through optimizing the above parameters, more than 70% or even more than 80% of the substrate conversion rate and the product yield may be achieved even in the scale-up production.

DETAILED DESCRIPTION OF THE EMBODIMENTS

It should be noted that embodiments in the present application and features in the embodiments may be combined with each other in the case without conflicting. The present disclosure is described in detail below in combination with the embodiments.

As analyzed in the background of the present application, the photocatalytic isomerization of the trans-cyclobutane-o-dicarboxylic acid ester compounds or the acid-catalyzed isomerization of the trans-cyclobutane-o-dicarboxylic acid ester compounds in the existing technology is difficult to achieve the scale-up production. In order to solve this problem, the present application provides a preparation method for a trans-cyclobutane-o-dicarboxylic acid ester and a derivative thereof. Since ring structures are prone to generate ring opening and elimination reactions under alkaline conditions, in order to achieve the isomerization of the trans-cyclobutane-o-dicarboxylic acid ester compounds, the applicant makes a systematic study on isomerization conditions and determines that the above isomerization may occur in organic alkali and a specific temperature range to avoid the ring opening or the elimination of a cyclobutane group. Therefore, the preparation method includes the following steps: in an organic solvent, catalyzing a substrate with a structure as shown in a structural formula I by using organic alkali at 50-90 DEG C. so as to generate isomerization, acquiring the trans-cyclobutane-o-dicarboxylic acid ester or the derivative thereof, herein the structural formula I is as follows:

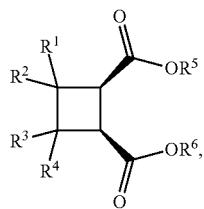

each of $R^1$, $R^2$, $R^3$ and $R^4$ is independently arbitrary one of hydrogen or an alkyl of $C_1$-$C_5$, and each of $R^5$ and $R^6$ is independently arbitrary one of alkyl of $C_1$-$C_{10}$ and benzyl.

The above isomerization process may refer to the following reaction formula:

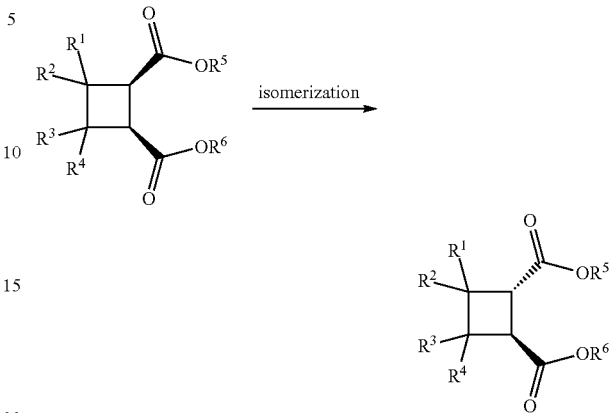

The present application uses the organic alkali as a catalyst to catalyze the trans-cyclobutane-o-dicarboxylic acid ester with the structural formula I or the derivative thereof at 50-90 DEG C. so as to generate an isomerization reaction, the process steps are shortened by one-step isomerization and efficient and simple. Reaction conditions are mild, and a special device is not required. Therefore, it is beneficial to scale-up production. Moreover, a substrate conversion rate and a product yield may be adjusted by adjusting the amount of reagents and the reaction temperature. Through optimizing the above parameters, more than 70% or even more than 80% of the substrate conversion rate and the product yield may be achieved even in the scale-up production.

The organic alkali used in the present application may be organic alkali that is often used as a catalyst in the existing technology. Preferably, the above organic alkali is selected from arbitrary one or more of alkoxide. The convenience of a source of a raw material is considered, preferably the alkoxide is sodium alkoxide and potassium alkoxide, further preferably the alkoxide is alkyl alkoxide of $C_1$-$C_5$, and more preferably the alkoxide is sodium methylate, sodium ethoxide, sodium tert-butoxide, and potassium tert-butoxide.

The amount of the above organic alkali may be set as the amount of the catalyst, and preferably a mole ratio of the above organic alkali and the substrate is 2.5:1-3.0:1.

In order to disperse and contact the above substrate and the catalyst more fully, preferably the above organic solvent is an alcohol solvent, and preferably the organic solvent is arbitrary one of methyl alcohol, ethyl alcohol, tert-butyl alcohol, and isopropyl alcohol. The alcohol solvent is a solvent commonly used in the field, and therefore it is more beneficial to an industrial scale-up production application of the preparation method of the present application. Moreover, while the above alcohol solvent and the above alkoxide are used in combination, the solubility of the alkoxide is relatively high, so the catalytic effect thereof is fully exerted.

A main function of the above organic solvent is to disperse the substrate and the organic alkali. In order to avoid the excessive amount of the organic solvent so that the concentration of the substrate and the organic alkali in a system to be reacted is too low and the reaction time is too long, preferably a volume ratio of the above organic solvent and the substrate is 2:1-5:1.

Those skilled in the art may set the temperature within the above temperature range according to the volatility performance and isomerization efficiency of the organic solvent used, preferably in the organic solvent, the organic alkali is used to catalyze the substrate to generate the isomerization at 60-80 DEG C., more preferably the organic alkali is used to catalyze the substrate to generate the isomerization at 65 DEG C. A mode of condensation and reflux may be used to avoid the volatilization of the solvent in a reaction process.

In an embodiment of the present application, the above preparation method includes the following steps: enabling the substrate to be dissolved in a part of the organic solvent, to form first solution; enabling the organic alkali to be dissolved in the other part of the organic solvent, to form second solution; after cooling the first solution to −5-10 DEG C., mixing with the second solution, to obtain a system to be reacted; and warming the system to be reacted to 60-70 DEG C. and heat-preserving for 1-3 hours so that the substrate generates the isomerization, to obtain a product system containing the trans-cyclobutane-o-dicarboxylic acid ester or the derivative thereof.

The organic alkali, the substrate and the organic solvent are mixed at a low temperature. On the one hand, it is beneficial to the full mixing of the materials, and on the other hand, the organic solvent is avoided from being unnecessarily volatilized in a mixing process.

In another embodiment of the present application, the above preparation method further includes the following steps: after cooling the product system to 20-30 DEG C., adjusting a pH value of the product system to 6-7, to obtain a quenching system; extracting the trans-cyclobutane-o-dicarboxylic acid ester or the derivative thereof in the quenching system by using an extracting agent, to obtain an extract; and removing the extracting agent in the extract, to obtain the trans-cyclobutane-o-dicarboxylic acid ester or the derivative thereof. After quenching, the trans-cyclobutane-o-dicarboxylic acid ester or the derivative thereof is separated from the product system by a mode of extraction, the operation is simple, and it is easy to the scale-up production.

The above adjustment of a pH value of the product system is achieved by adding an acid, preferably a diluted hydrochloric acid or a diluted nitric acid is used for adjusting the pH value of the product system, and a concentrated acid is not used in this process, so a large amount of three wastes catalyzed by the acid are not generated. The selection of the above extracting agent may be selected according to a difference between the solubility of the trans-cyclobutane-o-dicarboxylic acid ester or the derivative thereof to be separated and other substances in the extracting agent, and preferably the above extracting agent is arbitrary one of methyl tertiary butyl ether, n-hexane and dibutyl ether. The extracting agent in the above extract may be removed by a mode of spin-drying.

The above preparation method of the present application is suitable for the isomerization of the substrate with the structural formula I. Preferably, in the above structural formula I, the $R^1$, the $R^2$, the $R^3$ and the $R^4$ are the same and are the hydrogen or the methyl, and the $R^5$ and the $R^6$ are the same and selected from arbitrary one of the alkyl of $C_1$-$C_5$ and benzyl. The conversion rate of the substrate is improved.

The beneficial effects of the present application are further described below in combination with the embodiments and contrast examples.

Embodiment 1

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium methoxide/methanol solution with a concentration of 2.0 mol/L is dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 65 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a methyl tert-butyl ether (MTBE) to obtain an extract, the MTBE in the extract was spin-dried, and a nuclear magnetic resonance (NMR) internal standard method was used to detect 9.24 g of the cis-cyclobutane-o-dicarboxylic acid methyl ester. A reaction conversion rate was >98%, and a yield was 93%.

Embodiment 2

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium methoxide/methanol solution was dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 50 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 8.07 g of the cis-cyclobutane-o-dicarboxylic acid methyl ester. A reaction conversion rate was >85%, and a yield was 81%.

Embodiment 3

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium methoxide/methanol solution was dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 90 DEG C. and reacted for 2 h to obtain a product system. The product system was cooled to a room temperature, and a pH value of the product system is adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 8.44 g of the cis-cyclobutane-o-dicarboxylic acid methyl ester. A reaction conversion rate was >98%, and a yield was 85%.

Embodiment 4

After 10 g of a cis-cyclobutane-o-dicarboxylic acid methyl ester and 50 mL of methanol were mixed in a 250 mL

Embodiment 5

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium methoxide/methanol solution was dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 70 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 8.75 g of the cis-cyclobutane-o-dicarboxylic acid methyl ester. A reaction conversion rate was >98%, and a yield was 88%.

Embodiment 6

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium methoxide/methanol solution was dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 65 DEG C. and reacted for 1 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 8.57 g of the cis-cyclobutane-o-dicarboxylic acid methyl ester. A reaction conversion rate was >90%, and a yield was 86%.

Embodiment 7

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium methoxide/methanol solution was dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 65 DEG C. and reacted for 3 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 8.94 g of the cis-cyclobutane-o-dicarboxylic acid methyl ester. A reaction conversion rate was >98%, and a yield was 90%.

Embodiment 8

After 10 g of a cis-cyclobutane-o-dicarboxylic acid methyl ester and 30 mL of ethanol were mixed in a 250 mL four-necked flask (provided with a condenser pipe), the temperature was reduced to 0 DEG C., and then sodium ethoxide/ethanol solution was dropwise added to it, herein the amount of the sodium ethoxide was 3.0 times greater than a molar equivalent weight of the cis-cyclobutane-o-dicarboxylic acid methyl ester, and a system to be reacted was formed after addition. The system to be reacted was slowly heated to 65 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 9.25 g of the cis-cyclobutane-o-dicarboxylic acid methyl ester. A reaction conversion rate was >98%, and a yield was 93%.

Embodiment 9

After 10 g of a cis-cyclobutane-o-dicarboxylic acid methyl ester and 50 mL of tert-butyl alcohol were mixed in a 250 mL four-necked flask (provided with a condenser pipe), the temperature was reduced to 0 DEG C., and then sodium tert-butoxide/tert-butyl alcohol solution was dropwise added to it, herein the amount of the sodium tert-butoxide was 3.0 times greater than a molar equivalent weight of the cis-cyclobutane-o-dicarboxylic acid methyl ester, and a system to be reacted was formed after addition. The system to be reacted was slowly heated to 65 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 8.11 g of the cis-cyclobutane-o-dicarboxylic acid methyl ester. A reaction conversion rate was >85%, and a yield was 81%.

Embodiment 10

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium methoxide/methanol solution was dropwise added to it, herein the amount of the sodium methoxide was 2.5 times greater than a molar equivalent weight of the cis-cyclobutane-o-dicarboxylic acid methyl ester, and a system to be reacted was formed after addition. The system to be reacted was slowly heated to 65 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 9.28 g of the cis-cyclobutane-o-dicarboxylic acid methyl ester. A reaction conversion rate was >98%, and a yield was 93%.

Embodiment 11

A difference from Embodiment 1 was that a cis-cyclobutane-o-dicarboxylic acid ethyl ester was used to replace the cis-cyclobutane-o-dicarboxylic acid methyl ester. After being calculated, a reaction conversion rate was >98%, and a yield was 95%.

Embodiment 12

A difference from Embodiment 1 was that a cis-cyclobutane-o-dicarboxylic acid propyl ester was used to replace the cis-cyclobutane-o-dicarboxylic acid methyl ester. After being calculated, a reaction conversion rate was >97%, and a yield was 91%.

Embodiment 13

A difference from Embodiment 1 was that a cis-cyclobutane-o-dicarboxylic acid butyl ester was used to replace the cis-cyclobutane-o-dicarboxylic acid methyl ester. After being calculated, a reaction conversion rate was >95%, and a yield was 92%.

Embodiment 14

A difference from Embodiment 1 was that a cis-cyclobutane-o-dicarboxylic acid benzyl ester was used to replace the cis-cyclobutane-o-dicarboxylic acid methyl ester. After being calculated, a reaction conversion rate was >95%, and a yield was 90%.

Embodiment 15

After 1.0 kg of a cis-cyclobutane-o-dicarboxylic acid methyl ester and 5.0 L of methanol were mixed in a 25 L four-necked flask (provided with a condenser pipe), the temperature was reduced to 0 DEG C., and then sodium methoxide/methanol solution was dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 50 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 826 g of the cis-cyclobutane-o-dicarboxylic acid methyl ester. A reaction conversion rate was >88%, and a yield was 83%.

Contrast Example 1

After 1.0 kg of a cis-cyclobutane-o-dicarboxylic acid methyl ester and 5 L of methanol were mixed in a 20 L four-necked flask (provided with a condenser pipe), the temperature was reduced to 0 DEG C., and then sodium methoxide/methanol solution was dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 30 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 699 g of the cis-cyclobutane-o-dicarboxylic acid methyl ester. A reaction conversion rate was >80%, and a yield was 70%.

Contrast Example 2

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium methoxide/methanol solution was dropwise added to it, herein the amount of the sodium methoxide was 3.0 times greater than a molar equivalent weight of the cis-cyclobutane-o-dicarboxylic acid methyl ester, and a system to be reacted was formed after addition. The system to be reacted was slowly heated to 100 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 6.08 g of the cis-cyclobutane-o-dicarboxylic acid methyl ester. A reaction conversion rate was >79%, and a yield was 61%.

Contrast Example 3

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium hydroxide/methanol solution was dropwise added to it, herein the amount of the sodium hydroxide was 3.0 times greater than a molar equivalent weight of the cis-cyclobutane-o-dicarboxylic acid methyl ester, and a system to be reacted was formed after addition. The system to be reacted was slowly heated to 65 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 1.54 g of the cis-cyclobutane-o-dicarboxylic acid methyl ester. A reaction conversion rate was >97%, a yield was 15.4%, and about 80% was converted into an acid.

Contrast Example 4

After 10 g of a cis-cyclobutane-o-dicarboxylic acid methyl ester and 50 mL of methanol were mixed in a 250 mL four-necked flask (provided with a condenser pipe), the temperature was reduced to 0 DEG C., and then sodium hydrogen carbonate/methanol solution was dropwise added to it, herein the amount of the sodium hydrogen carbonate was 3.0 times greater than a molar equivalent weight of the cis-cyclobutane-o-dicarboxylic acid methyl ester, and a system to be reacted was formed after addition. The system to be reacted was slowly heated to 65 DEG C. and reacted for 2 h to obtain a product system. The product system was cooled to a room temperature, and a pH value of the product system was adjusted to 6-7 by using a diluted hydrochloric acid to obtain a quenching system. A trans-cyclobutane-o-dicarboxylic acid methyl ester in the quenching system was extracted by using a MTBE to obtain an extract, the MTBE in the extract was spin-dried, and a NMR internal standard method was used to detect 1.02 g of the cis-cyclobutane-o-dicarboxylic acid methyl ester. A reaction conversion rate was >35%, and a yield was 9.8%.

It may be seen from the above descriptions that the above embodiments of the present disclosure achieve the following technical effects:

The present application uses the organic alkali as a catalyst to catalyze the trans-cyclobutane-o-dicarboxylic acid ester with the structural formula I or the derivative thereof at 50-90 DEG C. so as to generate an isomerization reaction, the process steps are shortened by one-step isomerization and efficient and simple. Reaction conditions are mild, and a special device is not required. Therefore, it is beneficial to scale-up production. Moreover, a substrate conversion rate and a product yield may be adjusted by adjusting the amount of reagents and the reaction temperature. Through optimizing the above parameters, more than 70% or even more than 80% of the substrate conversion rate and the product yield may be achieved even in the scale-up production.

The above are only preferred embodiments of the present disclosure, and were not used to limit the present disclosure. For those skilled in the art, the present disclosure may have various modifications and changes. Any modifications, equivalent replacements, improvements and the like made within the spirit and principle of the present disclosure should be included in a scope of protection of the present disclosure.

What is claimed is:

1. A preparation method for a trans-cyclobutane-o-dicarboxylic acid ester, comprising:
   isomerizing a compound of formula I in an organic solvent at a temperature of 50-90° C. catalysed by an organic alkali to obtain the trans-cyclobutane-o-dicarboxylic acid ester, wherein the formula I is:

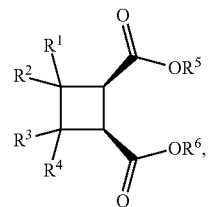

wherein:
   each of $R^1$, $R^2$, $R^3$ and $R^4$ is hydrogen, and each of $R^5$ and $R^6$ is selected from the group consisting of alkyl of $C_1$-$C_4$ and benzyl;
   the organic alkali is alkyl alkoxide of C1-C5;
   a mole ratio of the organic alkali and the compound is 2.5:1-3.0:1; and
   a volume ratio of the organic solvent and the compound is 2:1-5:1.

2. The preparation method according to claim 1, wherein the organic alkali is selected from the group consisting of sodium methylate, sodium ethoxide, sodium tert-butoxide, and potassium tert-butoxide.

3. The preparation method according to claim 1, wherein the organic solvent is an alcohol.

4. The preparation method according to claim 1, wherein the compound undergoes isomerization catalyzed by the organic alkali in the organic solvent at a temperature of 60-70° C.

5. The preparation method according to claim 1, wherein the preparation method comprises the following steps:
   dissolving the compound in a part of the organic solvent to form a first solution;
   dissolving the organic alkali in the other part of the organic solvent to form a second solution;
   cooling the first solution to −5-10° C. and then mixing it with the second solution to obtain a reaction system; and
   heating the reaction system to 60-70° C. and maintaining the temperature for 1-3 hours to induce isomerization of the compound, resulting in a product system containing the trans-cyclobutane-o-dicarboxylic acid ester.

6. The preparation method according to claim 5, wherein the preparation method further comprises the following steps:
   after cooling the product system to 20-30° C., adjusting a pH value of the product system to 6-7, to obtain a quenching system;
   extracting the trans-cyclobutane-o-dicarboxylic acid ester in the quenching system by using an extracting agent, to obtain an extract; and
   removing the extracting agent in the extract, to obtain the trans-cyclobutane-o-dicarboxylic acid ester.

7. The preparation method according to claim 6, wherein the pH value of the product system is adjusted by diluted hydrochloric acid or diluted nitric acid.

8. The preparation method according to claim 2, wherein the organic solvent is an alcohol.

9. The preparation method according to claim 2, wherein the preparation method comprises the following steps:
   dissolving the compound in a part of the organic solvent to form a first solution;
   dissolving the organic alkali in the other part of the organic solvent to form a second solution;
   cooling the first solution to −5-10° C. and then mixing it with the second solution to obtain a reaction system;

heating the reaction system to 60-70° C. and maintaining the temperature for 1-3 hours to induce isomerization of the compound, resulting in a product system containing the trans-cyclobutane-o-dicarboxylic acid ester.

10. The preparation method according to claim 3, wherein the preparation method comprises the following steps:
dissolving the compound in a part of the organic solvent to form a first solution;
dissolving the organic alkali in the other part of the organic solvent to form a second solution;
cooling the first solution to −5-10° C. and then mixing it with the second solution to obtain a reaction system;
heating the reaction system to 60-70° C. and maintaining the temperature for 1-3 hours to induce isomerization of the compound, resulting in a product system containing the trans-cyclobutane-o-dicarboxylic acid ester.

11. The preparation method according to claim 4, wherein the preparation method comprises the following steps:
dissolving the compound in a part of the organic solvent to form a first solution;
dissolving the organic alkali in the other part of the organic solvent to form a second solution;
cooling the first solution to −5-10° C. and then mixing it with the second solution to obtain a reaction system;
heating the reaction system to 60-70° C. and maintaining the temperature for 1-3 hours to induce isomerization of the compound, resulting in a product system containing the trans-cyclobutane-o-dicarboxylic acid ester.

12. The preparation method according to claim 1, wherein the organic solvent is selected from the group consisting of methyl alcohol, ethyl alcohol, tert-butyl alcohol, and isopropyl alcohol.

13. The preparation method according to claim 7, wherein the extracting agent is selected from the group consisting of methyl tertiary butyl ether, n-hexane or dibutyl ether.

14. The preparation method according to claim 2, wherein the organic solvent is selected from the group consisting of methyl alcohol, ethyl alcohol, tert-butyl alcohol, and isopropyl alcohol.

* * * * *